United States Patent
Collick et al.

[11] Patent Number: 6,097,977
[45] Date of Patent: Aug. 1, 2000

[54] METHOD FOR CONTROLLING DATA ACQUISITION AND IMAGE RECONSTRUCTION DURING CONTINUOUS MR IMAGING

[75] Inventors: Bruce D. Collick, Madison; Michael R. Hartley, Pewaukee, both of Wis.

[73] Assignee: General Electric Company, Milwaukee, Wis.

[21] Appl. No.: 09/001,900

[22] Filed: Dec. 31, 1997

[51] Int. Cl.[7] ............................................. A61B 5/055
[52] U.S. Cl. ........................ 600/410; 324/309; 382/128; 128/922
[58] Field of Search ............................. 600/410; 324/307, 324/309; 382/128; 128/920, 922

[56] References Cited

U.S. PATENT DOCUMENTS

| | | | |
|---|---|---|---|
| 4,949,041 | 8/1990 | Zur | 324/309 |
| 5,184,074 | 2/1993 | Kaufman et al. | 324/309 |
| 5,531,227 | 7/1996 | Schneider | 600/407 |
| 5,653,233 | 8/1997 | Pelc et al. | 600/410 |
| 5,779,636 | 7/1998 | Kanzawa | 600/410 |
| 5,833,609 | 11/1998 | Dannels et al. | 600/410 |
| 5,924,987 | 7/1999 | Meaney et al. | 600/420 |
| 5,933,006 | 8/1999 | Rasche et al. | 324/307 |

*Primary Examiner*—Brian L. Casler
*Attorney, Agent, or Firm*—Quarles & Brady; Christian G. Cabou; Phyllis Y. Price

[57] ABSTRACT

An MRI system performs a real-time scan in which image frames are produced as the image is moved to different locations in the patient. The location at which each set of image data is acquired is compared, and image data acquired at the same location are combined to improve image quality. An autonex feature enables averaging of successive image data acquisitions and a frame rate feature enables combining of partial NEX acquisitions.

11 Claims, 3 Drawing Sheets

METHOD FOR CONTROLLING DATA ACQUISITION AND IMAGE RECONSTRUCTION DURING CONTINUOUS MR IMAGING

BACKGROUND OF THE INVENTION

The field of the invention is nuclear magnetic resonance imaging methods and systems. More particularly, the invention relates to the acquisition of MRI data during a real-time acquisition mode in which the operator can change the location of the image acquisition as the scan is being performed.

When a substance such as human tissue is subjected to a uniform magnetic field (polarizing field $B_0$), the individual magnetic moments of the spins in the tissue attempt to align with this polarizing field and precess about it with random phase at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

The present invention will be described in detail with reference to a variant of the well known Fourier transform (FT) imaging technique, which is frequently referred to as "spin-warp". The spin-warp technique is discussed in an article entitled "Spin-Warp NMR Imaging and Applications to Human Whole-Body Imaging" by W. A. Edelstein et al., *Physics in Medicine and Biology*, Vol. 25, pp. 751–756 (1980). It employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one direction by applying a phase encoding gradient ($G_y$) along that direction, and then a spin-echo signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($\Delta G_y$) in the sequence of views that are acquired during the scan to produce a set of NMR data from which an entire image can be reconstructed.

In the real-time acquisition mode, MR images are continuously acquired and the operator can change the spatial location of the image dynamically. This is accomplished by manually entering a new image location or by using the location produced by a position transducer such as that disclosed in U.S. Pat. Nos. 5,617,857 and 5,622,170. Each image acquisition is comprised of a series of views (e.g. 256) in which the phase encoding is stepped through a series of values to sample k-space in a specified order. When using a fast gradient-recalled echo 2DFT pulse sequence, for example, a complete image acquisition may require 0.1 to 0.5 seconds.

To increase the rate at which image frames are acquired, image quality may be sacrificed by acquiring fewer phase encoding views, or by using faster pulse sequences that inherently result in lower quality images. This sacrifice in image quality is a trade-off for the increased motion artifacts that appear in the images if the image frame rate is slower.

SUMMARY OF THE INVENTION

The present invention is a method for automatically altering the number of views acquired for each image frame as a function of image location. More particularly, a specified number of k-space views are acquired for each image frame, the location of the image is checked, and if the image location is unchanged, the specified number of acquired k-space views are combined with previously acquired views to improve the quality of the reconstructed image. The specified k-space views may be the same views during each acquisition and they may be combined with previous acquisitions by averaging corresponding views. Different portions of k-space may be acquired during each acquisition and the views from successive acquisitions may be combined to form a more complete sampling of k-space.

A general object of the invention is to improve the quality of MR images produced during a real-time scan in which image location is unchanged. The image frame reconstruction rate is set to match the maximum image location update rate. This may require the use of very fast pulse sequences, or the acquisition of less than a full set of views (i.e. partial NEX), or both. The present invention recognizes that when the image frame is not being moved between successive image frame acquisitions, the views acquired during successive acquisitions can be combined to improve image quality. As a result, the operator can move the image location until it is precisely aligned with the clinically interesting structures, and then higher quality images are automatically acquired from that structure merely by maintaining that location over a plurality of image frame acquisitions.

DESCRIPTION OF THE PREFERRED EMBODIMENT

Figure 1:
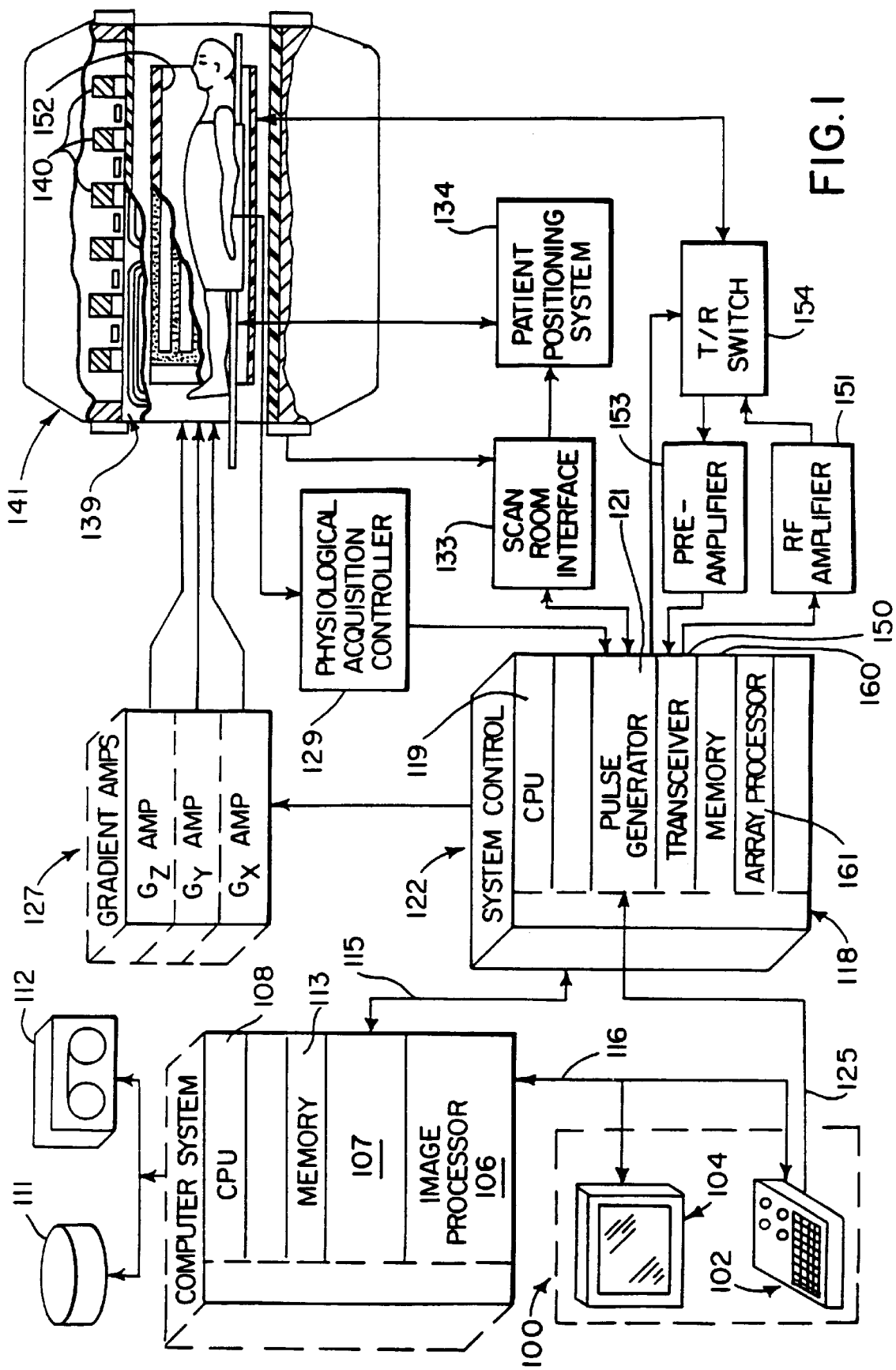
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or position information from a position transducer (not shown) attached to the patient. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

For a more detailed description of the transceiver 150, reference is made to U.S. Pat. Nos. 4,952,877 and 4,922,736 which are incorporated herein by reference.

The MRI system can be operated in a real-time control mode in which the location from which images are acquired can be manually changed during the scan. Such manual position information is input by an operator through the control panel 102. In the alternative, some MRI systems operate in an interactive mode in which a position transducer may be located on or near the patient and it directs the MRI system to acquire image frames from locations that track the movement of the transducer during the scan. In either case, the selected pulse sequence is repeatedly performed under the direction of the pulse generator module 121 which receives position information from either the control panel 102 or directly from the position transducer system. The pulse generator module 121 alters the pulse sequence by changing the amplitude of gradient pulses and/or the frequency of RF excitation pulses to acquire image data from the newly directed location.

Figure 2:
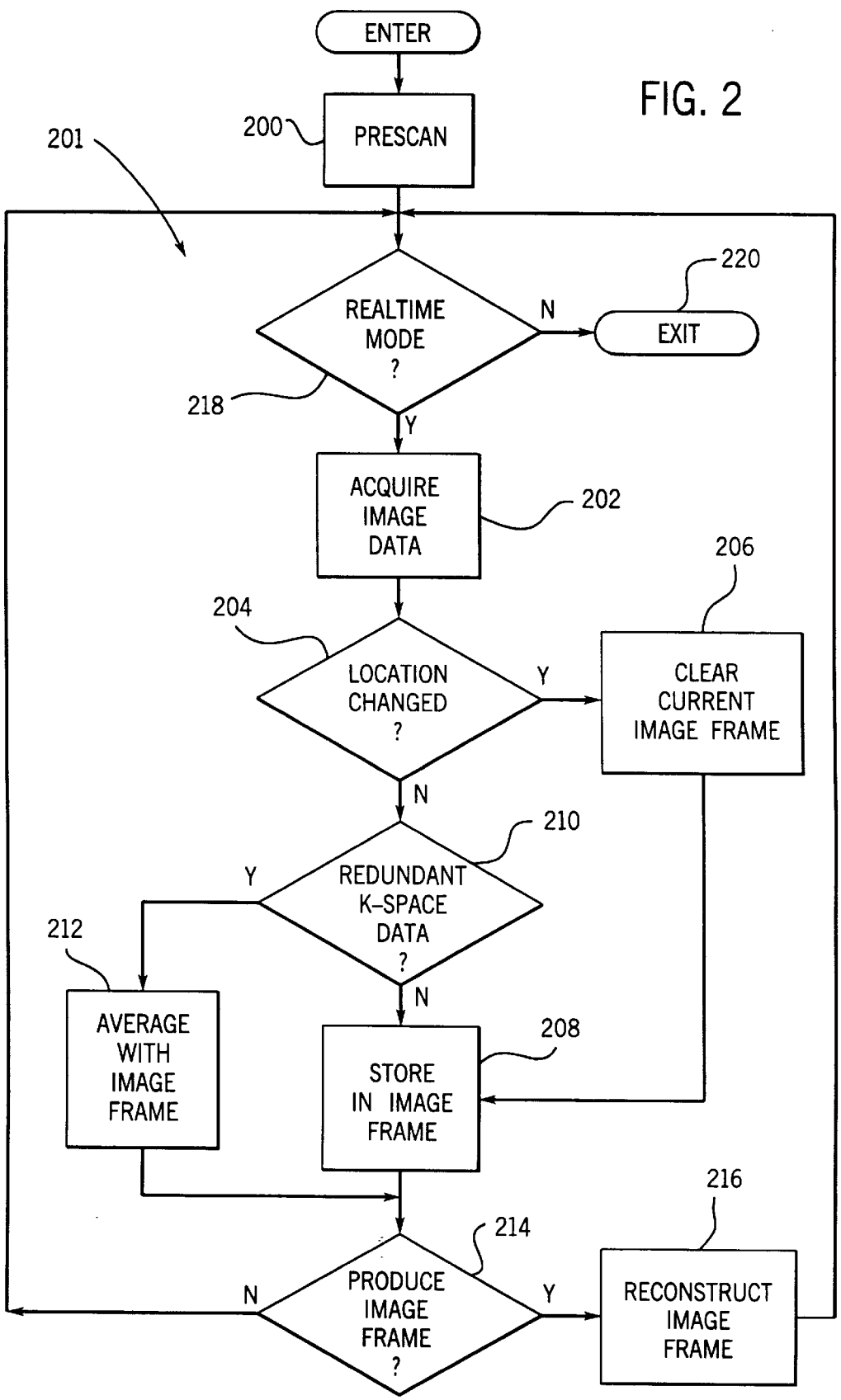
FIG. 2 is a flow chart of the real-time scan process performed by the MRI system of FIG. 1 according to the preferred embodiment of the invention.

Referring particularly to FIG. 2, when the MRI system is operating in the real-time mode a prescan is performed as indicated at process block 200 and then it enters a loop indicated generally at 201 in which image acquisitions are performed as fast as possible using the prescribed pulse sequence. More specifically, image data is acquired at process block 202 and a check is made at decision block 204 to determine if the data was acquired at the same spatial location as during the previous pass through the real-time control loop 201. The image acquisition 202 may be either a complete or partial sampling of k-space depending on the prescribed scan. If the location has changed, the buffer memory which stores the current image frame data is cleared at process block 206, and the newly acquired image data is stored therein as indicated at process block 208. On the other hand, if the location of the acquisition has not changed, a test is made at decision block 210 to determine if the newly acquired image data is redundant to that already stored in the image frame buffer. This will depend on the particular scan strategy prescribed by the operator as will be explained in more detail below. If it is not redundant, the newly acquired image data is stored in the image frame buffer at process block 208. If it is redundant, however, the newly acquired image data is averaged with that already stored in the image frame buffer, as indicated at process block 212.

The next step in the real-time process is to determine if an image should be produced, as indicated at decision block 214. There are two circumstances which indicate that an image is to be produced. First, if the data in the image frame buffer is complete in the sense that all of k-space has been sampled, an image is reconstructed as indicated at process block 216. In addition, the operator can prescribe a minimum frame rate and if the time interval has expired since the last image frame was produced, an image frame is reconstructed at process block 216. In the latter case, k-space sampling may be incomplete, and either zero-filling or a homodyne reconstruction may be used during the reconstruction process.

The real-time process continues and image frames are produced until the operator switches modes. This is detected at decision block 218 and the real-time process exits at 220.

The real-time process according to the preferred embodiment enables a number of imaging strategies to be implemented. First, it enables image quality to be significantly improved when the spatial location remains fixed for a number of acquisitions using an "autonex" feature. When the autonex feature is enabled, the operator selects how many image acquisitions may be averaged before an image is reconstructed. When the real time scan is performed, the most recent images acquired at the same location are averaged up to this number. This technique is illustrated in Table A when a series of images are acquired at the same location with an autonex value of "3".

TABLE A

| Image Frame No. | Acquired Image Data | Reconstructed Image |
|---|---|---|
| 1 | $R_1$ | $R_1$ |
| 2 | $R_2$ | $R_1 + R_2/2$ |
| 3 | $R_3$ | $R_1 + R_2 + R_3/3$ |
| 4 | $R_4$ | $R_2 + R_3 + R_4/3$ |
| 5 | $R_5$ | $R_3 + R_4 + R_5/3$ |

Table B illustrates the operation of the autonex feature when the image location changes at image frame numbers 6 and 8 during the real-time scan.

TABLE B

| Image Frame No. | Acquired Image Data | Reconstructed Image |
|---|---|---|
| 1 | $R_1$ | $R_1$ |
| 2 | $R_2$ | $R_1 + R_2/2$ |
| 3 | $R_3$ | $R_1 + R_2 + R_3/3$ |
| 4 | $R_4$ | $R_2 + R_3 + R_4/3$ |
| 5 | $R_5$ | $R_3 + R_4 + R_5/3$ |
| Movement | | |
| 6 | $R_6$ | $R_6$ |
| 7 | $R_7$ | $R_6 + R_7/2$ |
| Movement | | |
| 8 | $R_8$ | $R_8$ |
| 9 | $R_9$ | $R_8 + R_9/2$ |
| 10 | $R_{10}$ | $R_8 + R_9 + R_{10}/3$ |

The averaging performed using the autonex feature is done on the k-space data sets in the preferred embodiment described above. The averaging is performed at process block 212 and it is done on the most recently acquired image data sets, up to the selected autonex value as indicated above in Tables A and B.

The averaging can also be done after image reconstruction. In this alternative embodiment each acquired image is reconstructed and saved. The autonex feature is then implemented by averaging the pixel values in the reconstructed images as indicated above in Tables A and B. In this alternative embodiment the image reconstruction process is performed in the usual manner and autonex is implemented as a post-processing display step in which the appropriate stored images are averaged.

Another imaging strategy which the preferred embodiment implements is a frame rate feature. This feature enables the operator to prescribe the rate at which new images are reconstructed. The prescribed frame rate sets a timer which is checked at decision block 214. If the interval since the last image frame reconstruction exceeds this preset value, an image is reconstructed using the currently available image data acquired since the last location change.

In this mode, if the reconstruction rate is faster than the complete image acquisition rate, the first images at a new location would have either poor contrast or poor edge definition due to incomplete k-space sampling. If no movement occurs, image quality would gradually improve until a full raw data set was acquired. The choice of whether poor contrast or poor edge definition would occur during motion is determined by the data acquisition scheme. As a general rule, data at the center of k-space provides image contrast information and the data at the periphery of k-space provides edge definition. There are a wide variety of data acquisition strategies that can provide variable performance. Regardless of the selected data acquisition strategy, the present invention enables the operator to achieve the desired frame rate to follow rapid changes in location or patient motion, and at the same time enables high quality images to be acquired when the image location remains fixed for a number of frames.

Figure 3:
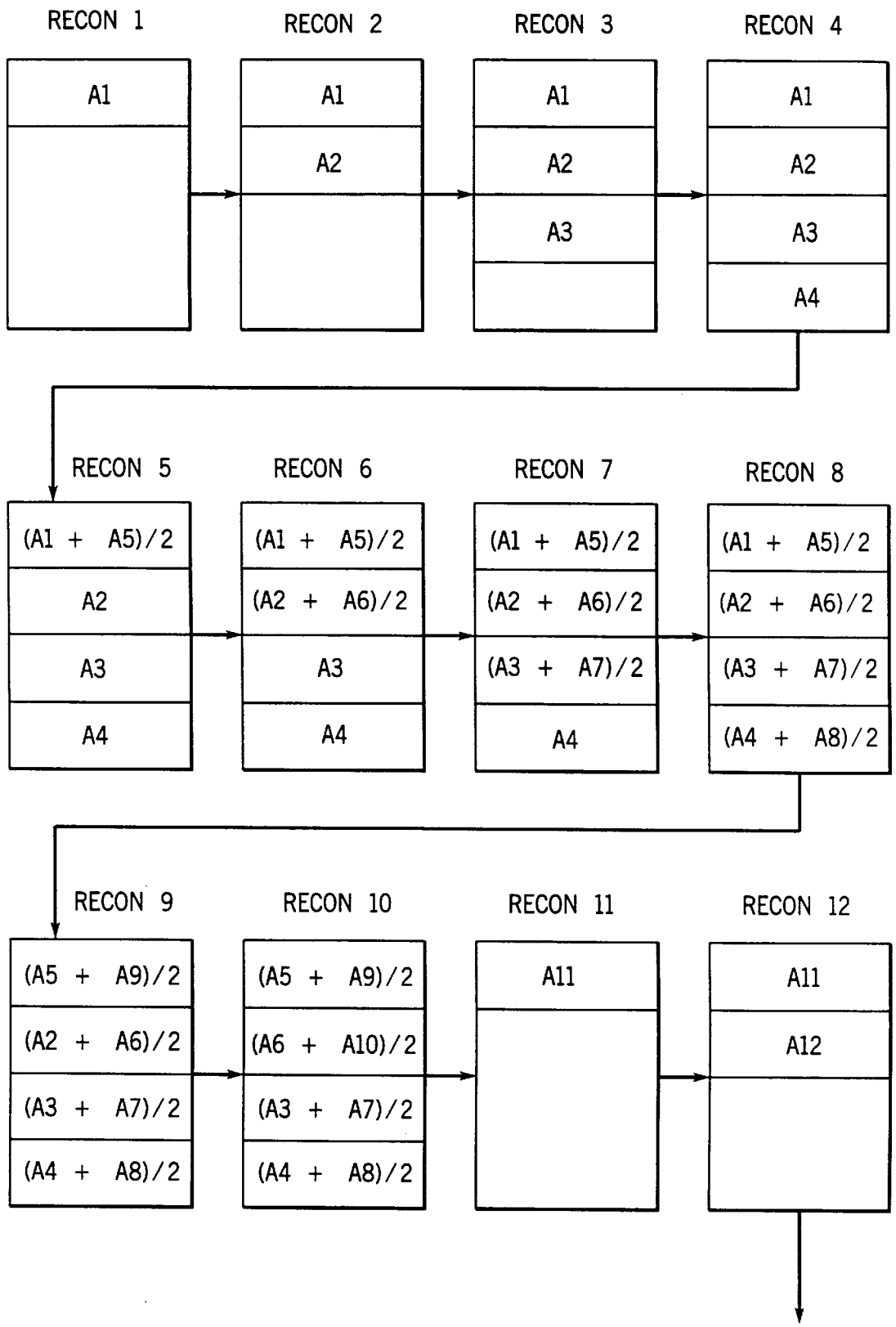
FIG. 3 is a pictorial representation of an example image reconstruction sequence performed during the real-time scan process.

FIG. 3 illustrates the use of the autonex feature to improve image quality of partial nex acquisitions during continuous scanning. In this particular example, the autonex feature is set to accumulate and average data over eight consecutive acquisitions. Each partial nex acquisition covers a fraction of k-space (e.g. one-fourth of k-space), and an image frame is reconstructed after each acquisition as illustrated for reconstructions 1 through 4. The image quality improves as the raw data from each successive acquisition is accumulated with data from the previous acquisitions. After four acquisitions the full range of k-space has been accumulated. The autonex feature continues to accumulate and average the partial nex data for subsequent acquisitions as illustrated for reconstructions 5 through 8. After the eighth acquisition the raw data is equivalent to a 2 nex full k-space acquisition. At this point each successive partial nex acquisition will result in a reconstruction of an image from a 2 nex full k-space raw data set. After the tenth acquisition in this example, there is movement and the image frame buffer is cleared.

What is claimed is:

1. A method for producing a series of image frames during an MR scan, the steps comprising:
   a) acquiring an image data set from a location using an MRI system;
   b) detecting the location from which the image data set was acquired;
   c) storing the acquired image data set as a set of values in a frame buffer memory;
   d) repeating steps a) and b) to acquire a new image data set of values;
   e) comparing the location from which the new image data set was acquired with the location from which the previous image data set was acquired, and based on the results of this comparison either
      i combining the new image data set with the data set stored in the frame buffer memory if the compared locations are substantially the same, or
      ii storing the new image data set in another frame buffer memory if the compared locations are substantially different;
   f) repeating steps d) and e); and
   g) producing image frames for display from the image data stored in the frame buffer memories as the MR scan is performed.

2. The method as recited in claim 1 in which the new image data set is combined in step e) i) with the data set stored in the frame buffer memory by averaging the corresponding values thereof.

3. The method as recited in claim 1 in which the image frames are produced at a prescribed frame rate during the scan.

4. The method as recited in claim 1 in which the frame buffer memory stores k-space image data sets and image frames are produced by reconstructing images from the k-space image data sets.

5. The method as recited in claim 1 in which the frame buffer memory stores k-space image data sets having values which represent samples at locations in k-space and the new image data set is combined in step e) i) with the data stored in the frame buffer by adding the new image data set to previously unsampled locations in k-space.

6. A magnetic resonance imaging system for producing a series of image frames during an MR scan of a subject, which comprises:

a) a magnet for producing a polarizing magnetic field in the subject;
b) means for producing magnetic field gradients in the subject;
c) rf means for producing an rf excitation field in the subject and acquiring NMR signals produced by spins in the subject;
d) a pulse generator which operates elements b) and c) to repeatedly perform a prescribed pulse sequence and to thereby acquire NMR signals from a field of view in the subject;
e) means for directing the pulse generator to change the field of view from which NMR signals are being acquired;
f) means for processing acquired NMR signals to produce image data;
g) image reconstruction and display means for producing at intervals during the MR scan images using image data stored in a frame buffer memory;
h) means for combining newly acquired image data with image data stored in the frame buffer memory as long as the field of view remains substantially unchanged; and
i) means for clearing the image frame buffer memory when the field of view is substantially changed.

7. The magnetic resonance imaging system as recited in claim 6 in which the means for combining newly acquired image data averages the newly acquired image data with corresponding image data stored in the frame buffer.

8. The magnetic resonance imaging system as recited in claim 6 in which the image data stored in the frame buffer memory is comprised of k-space data and the means for combining newly acquired image data fills in missing k-space data until all of k-space has been acquired, and then it averages further newly acquired image data with corresponding image data stored in the frame buffer.

9. The magnetic resonance imaging system as recited in claim 6 in which the image reconstruction and display means periodically produces an image using the image data stored in the frame buffer memory.

10. The magnetic resonance imaging system as recited in claim 9 in which the image data stored in the frame buffer memory is k-space data and the image reconstruction and display means includes means for performing a Fourier transformation of the k-space data.

11. The magnetic resonance imaging system as recited in claim 6 in which the means for changing the field of view includes a control panel through which field of view information may be entered.

* * * * *